US007717962B2

(12) United States Patent
Wilson

(10) Patent No.: US 7,717,962 B2
(45) Date of Patent: May 18, 2010

(54) PROPRIOCEPTION ENHANCEMENT DEVICE

(76) Inventor: Michael T. Wilson, 2711 Cartwright Rd., Missouri City, TX (US) 77459

( * ) Notice: Subject to any disclaimer, the term of this patent is extended or adjusted under 35 U.S.C. 154(b) by 1092 days.

(21) Appl. No.: 11/277,199

(22) Filed: Mar. 22, 2006

(65) Prior Publication Data

US 2009/0069898 A1 Mar. 12, 2009

(51) Int. Cl.
*A61F 2/48* (2006.01)
*A61B 5/103* (2006.01)
(52) U.S. Cl. ............................. 623/24; 623/53; 600/595
(58) Field of Classification Search ................. 600/595; 623/24, 27, 44, 53–56; 73/172
See application file for complete search history.

(56) References Cited

U.S. PATENT DOCUMENTS

| 3,984,100 | A | | 10/1976 | Firster |
| 4,186,920 | A | | 2/1980 | Fiore et al. |
| 4,635,932 | A | | 1/1987 | Dewees |
| 4,653,748 | A | | 3/1987 | Seel et al. |
| 4,739,986 | A | | 4/1988 | Kucharik et al. |
| 5,035,421 | A | | 7/1991 | Scheller |
| 5,062,856 | A | | 11/1991 | Sawamura et al. |
| 5,112,045 | A | | 5/1992 | Mason et al. |
| 5,252,102 | A | * | 10/1993 | Singer et al. .................. 623/24 |
| 5,253,656 | A | | 10/1993 | Rincoe et al. |
| 5,368,536 | A | | 11/1994 | Stodgell |
| 5,413,611 | A | * | 5/1995 | Haslam et al. ................. 623/25 |
| 5,603,334 | A | | 2/1997 | Sharp |
| 5,613,690 | A | | 3/1997 | McShane et al. |
| 5,810,703 | A | | 9/1998 | Stack |
| D405,135 | S | | 2/1999 | Scott |
| 5,891,002 | A | | 4/1999 | Maki |
| 5,893,891 | A | * | 4/1999 | Zahedi ......................... 623/24 |
| 5,897,474 | A | | 4/1999 | Romero |
| 6,273,863 | B1 | | 8/2001 | Avni et al. |
| 6,436,058 | B1 | * | 8/2002 | Krahner et al. .............. 600/587 |
| 6,679,920 | B2 | * | 1/2004 | Biedermann et al. .......... 623/24 |
| 6,692,449 | B1 | * | 2/2004 | Brown ........................ 600/595 |
| 6,811,523 | B1 | | 11/2004 | Timmer |
| 7,147,667 | B2 | * | 12/2006 | Bedard ........................ 623/24 |
| 2002/0143405 | A1 | * | 10/2002 | Davalli et al. ................. 623/24 |
| 2007/0203435 | A1 | * | 8/2007 | Novak ......................... 601/70 |

OTHER PUBLICATIONS

International Search Report and Written Opinion dated Nov. 20, 2007 for International Appl. No. PCT/US07/64527 (7 p.).

* cited by examiner

*Primary Examiner*—Bruce E Snow
(74) *Attorney, Agent, or Firm*—Conley Rose, P.C.

(57) ABSTRACT

A system and method for improving proprioception in a patient having a feedback site are disclosed. The method includes affixing to the feedback site a sensor adapted to provide a sensor signal indicative of a sensed parameter, providing to the patient a signaler adapted to generate a manual signal in response to actuation by the patient, providing a microprocessor programmed to receive the sensor signal and the manual signal and to generate a system output based on the sensor signal and the manual signal, causing the patient to actuate the signaler on the basis of sensation at the feedback site, and causing the microprocessor to generate a system output based on the sensor signal and the manual signal.

8 Claims, 1 Drawing Sheet

PROPRIOCEPTION ENHANCEMENT DEVICE

CROSS-REFERENCE TO RELATED APPLICATIONS

Not Applicable.

STATEMENT REGARDING FEDERALLY SPONSORED RESEARCH OR DEVELOPMENT

Not Applicable.

FIELD OF THE INVENTION

The present invention relates generally to a device that can be used to provide biosensory feedback that would not otherwise be available to an individual, so that the individual can gain increased ability to move his or her natural and/or prosthetic limbs. More particularly, the present invention provides a means for providing feedback that can allow an individual to better recognize and distinguish between perception of various body movements or positions.

BACKGROUND OF THE INVENTION

Proprioception involves neuromuscular receptors in the skeletal muscles and on the surface of the tendons. These receptors provide constant feedback to the brain regarding movement, posture, changes in equilibrium, knowledge of position, weight, and resistance against its body parts. Using this feedback, the brain is typically able to correct or adapt to changes in these parameters. Amputees, and particularly amputees who have been fitted with prostheses, must learn to move their natural and prosthetic limbs without the benefit of proprioceptive feedback from the limb that is no longer present.

In cases of limb amputation, it is typically necessary for the amputee to undergo rehabilitation in order to regain functionality that is as close to normal as possible. In particular, if the amputated limb is replaced with a prosthesis, it is necessary for the amputee to learn to use the prosthesis in a way that will maximize restored functionality. The rehabilitation prescribed in such cases is designed to modify the amputee's proprioception such that he or she learns to use the prosthesis in a manner that approximates that of the lost limb.

At the same time, amputees often sense that the amputated limb is still present. This is known as Phantom Limb Syndrome. Phantom sensations can occur as passive proprioceptive sensations of the limb's presence, or more active sensations such as perceived movement, pressure, pain, itching, or temperature. The etiology of the phantom limb phenomenon is not well understood; both neurological and psychological explanations have been postulated. The sensations can be distressing, and patients are often counseled to ignore or suppress them.

Still further, after many types of major surgery, including amputation, moderate forms of exercise are prescribed as beneficial to the healing process. Exercise that directly affects the wounded area, e.g. amputation cite, while particularly helpful for increasing blood flow and reducing atrophy and stiffening, also brings associated risks of increasing damage to the wounded tissue, such as through trauma or excessive stress.

It would be advantageous to provide a device that allows an amputee to re-direct and use the sensory perceptions associated with a phantom limb in re-establishing proprioception with respect to his or her prosthesis. It would also be desirable to provide a system that allows an amputee to obtain the benefits of exercise and a desired level of vaso-stimulation without risking tissue damage.

SUMMARY OF THE INVENTION

The present invention includes a device and system that allow an amputee to re-direct and use sensory perceptions, including those associated with a phantom limb, in re-establishing proprioception with respect to his or her prosthesis. In certain embodiments, the present invention features a device adapted to engage a prosthesis and to provide sensory feedback when certain events or physical standards are met.

The present invention comprises a combination of features and advantages which enable it to overcome various problems of prior devices. The various characteristics described herein, as well as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of the preferred embodiment of the present invention, reference will now be made to the accompanying drawing, which is an illustration of a system constructed in accordance with a first embodiment of the present invention.

DETAILED DESCRIPTION OF THE PREFERRED EMBODIMENT

Figure 1:
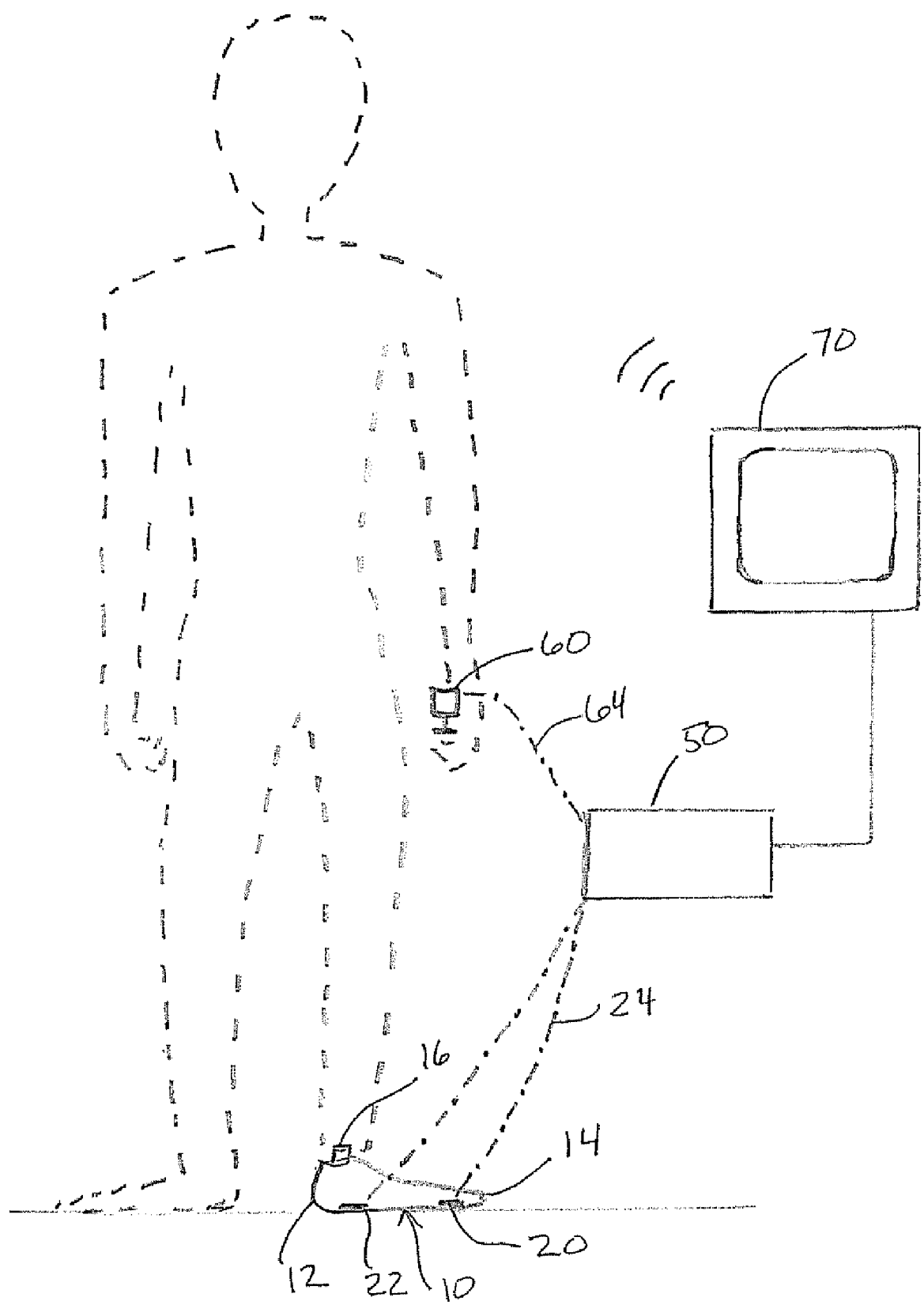

Referring initially to FIG. 1, an exemplary system in accordance with the present invention, includes a prosthetic foot 10, a microprocessor 50, a signaler 60, and an output device 70. Prosthetic foot 10 typically will include a heel 12, a toe 14, and an attachment member 16. Prosthetic foot 10 can be any type of prosthetic foot, such as are generally known in the art Likewise, attachment member 16 may comprise a standard "Otto Bock"-type connector, such as are commercially available, or may comprise any other attachment means that can serve to attach the foot to the amputee.

According to certain embodiments, foot 10 includes at least one, and preferably two or more sensors 20, 22. Sensors 20, 22 are preferably low-profile, highly-accurate pressure sensors, such as are readily commercially available. Both sensors are positioned on the bottom of the prosthesis, so that they contact the ground when the wearer puts pressure on (stands on), the prosthetic foot. One sensor, forward sensor 20, may be positioned tinder the forward portion of the foot, while the other sensor, rear sensor 22, may be positioned under the heel of the foot. Sensors 20, 22 are preferably coupled to a microprocessor 50 so that sensor signals 24 representative of pressure sensed by each sensor can be received and processed by microprocessor 50. For example, sensors 20, 22 may be wired to microprocessor 50 or may be connected to a wireless transmitter (not shown), such as an infra-red transmitter, which transmits the signal to a corresponding receiver, which receives the signal and sends it to the microprocessor. Means for transmitting signals are known.

When foot 10 including sensors 20 and 22 is worn and used, sensors 20, 22 will sense pressure loads that correspond to the gait of the wearer. According to embodiments of the invention, information relating to these loads can be processed and sent to the wearer in a manner that enables the wearer to increase his rate of healing. Specifically, it is envisioned that the system will be programmed to give the wearer feedback relating to the magnitude, positioning and timing of the loads on the foot.

In order to give the wearer information about the magnitude various techniques may be used. In each case, the signal from at least one of the sensors is converted by microprocessor 50 into an output that represents the amount of pressure (weight) that is applied to the foot. If two or more sensors are used, it is preferred to obtain the magnitude of the total pressure by summing the signals from all of the sensors.

In certain embodiments, microprocessor 50 may be programmed to compare the magnitude of the pressure applied to the prosthesis to a predetermined target value. In these embodiments, the microprocessor output may include triggering an audible or visible indicator when the target value is reached. In other embodiments, the microprocessor output may include an audible or visible signal corresponding to the measured value. For example, the microprocessor may be connected to a digital or analog output device 70 that indicates numerically or graphically the magnitude of the pressure being applied to the foot. Alternatively, the output may comprise an audible signal that indicates through pitch or volume the magnitude of the applied pressure.

In other embodiments, the wearer may be further equipped with a signaler 60, which may include means for manually sending a signal to the microprocessor. Signaler 60 may include a belt-pack and finger switch, or the like, such as are readily commercially available. It will be understood that the terms "manual" and "finger" are not intended to limit the device; the system can include any device that can send signal in response to actuation by the patient. A signal 64 sent by signaler 60 in response to actuation by the patient will be referred to hereinafter as a "manual signal."

In these embodiments, microprocessor 50 may be programmed to monitor the magnitude of the pressure applied to the prosthesis. For example, microprocessor 50 may be programmed to provide an indication when the actual (detected) load is the same as, or within a predetermined range of, a target value. Alternatively, the microprocessor can provide to the wearer feedback that is indicative of the magnitude of the difference, if any, between the actual load and the target value.

In some embodiments, an objective therapeutic goal would be for the wearer to achieve sufficient proprioception to be able to correctly sense target weight loads. In these cases, the wearer may be instructed to manually actuate signaler 60 when he or she believes that a predetermined target pressure is being applied. By comparing the measured or detected weight at the time that manual signal is given to the target weight, the system can provide feedback to the wearer, indicating the difference between the two.

In some embodiments, the wearer is again outfitted with a signaler, but the microprocessor is programmed to calculate a projected time for reaching the target value. Using the projected time calculation and the existing time and magnitude, the microprocessor can output a signal that is indicative of the amount of time by which the wearer's manual signal is premature or late. For example, the system can be programmed to give a visual or audible signal such as "1 second early" or "½ second late." Other means of indicating the relative timing of the manual signal and the target pressure may include timed tones, timed lights, digital readouts, and the like. The manual signal can be compared to either an extrapolation of the measured signal, which is particularly useful when the manual signal precedes the target pressure, or on a measurement of the actual pressure, which is more accurate. Measurement of the actual pressure can only be used if the target pressure is actually reached, either before or after the manual signal is given. If the feedback is based on an extrapolation of the measured signal, the microprocessor preferably uses the rate of increase in the load during the period that the load is increasing to determine when the target load would have been reached if loading had continued at that rate. Thus, in these embodiments, the system is programmed to calculate rate as well as magnitude and timing of load.

In still other embodiments, the prosthesis may be adapted to provide the wearer with feedback relating to the position of the prosthesis relative to the wearer. In some embodiments, the position of the prosthesis is determined by comparing the relative magnitudes of the signals from the two sensors 20, 22, and using the ratio to determine position. For example, as the prosthesis is moved forward, away from the wearer, the load on the rear sensor 22 will increase relative to the load on the front sensor 20. The ratio of the loads on sensors 20, 22 can be compared to a look-up table or otherwise calibrated so as to provide information relating to the position of the prosthesis relative to the wearer. Front and rear sensors 20, 22 can provide information about the positioning of the prosthesis in front of or behind the wearer; lateral positioning, i.e. to the left or right of the wearer, if desired, can be provided by providing at least one sensor that is shifted laterally with respect to a second sensor. By way of example, an optional third sensor (not shown) can be added beside or between sensors 20, 22, so long as it does not lie on a line between sensors 20, 22. In other embodiments, the prosthesis may include other types of sensors, such as position sensors, infra-red sensors, accelerometers, or inclinometers, that are adapted to provide the information that can be used in the enhancement of proprioception.

As with the magnitude and timing feedbacks, position feedback can be given by various audible or visible means. In preferred embodiments, the wearer may manually signal when he or she believes that the prosthesis is in a predetermined target position and the system will indicate whether the manual signal is early or late and/or the degree to which the wearer is in error.

The sensors described herein can be incorporated into or adhered onto a prosthetic foot, which may be a standard prosthetic foot or a prosthesis that is customized for a particular patient. Similarly, the sensors can be incorporated into a shoe, sock or slipper that can be applied to any prosthetic foot. As used herein, the term "shoe" encompasses all such terms and all other items that can be worn on a foot. It is envisioned that a shoe equipped with sensing and feedback mechanisms as described herein could also be used with a natural foot, if it were desired to provide such feedback to a non-amputee. Such might be the case, for instance, in cases of nerve damage that prevents the patient from sensing his own limb(s). It will thus be understood that the sensors of the present invention are not limited to use in the context of prosthetic feet or to use by amputees. Rather, they can be applied to any site where it is desired to provide proprioceptive feedback. The feedback site may be any site on the patient's body. In the case of an amputee, the feedback site will typically be the terminus of the remaining partial limb. Likewise, it will be understood that the sensors can be affixed to the feedback site indirectly, such as by means of a prosthesis or shoe, or directly, such as by direct adhesion.

By providing quantitative feedback indicative of the accuracy of the patient's proprioception, the present system provides a mechanism for enhancing that proprioception. This is in contrast to many existing systems, which provide little or no feedback. In addition, the present system can be programmed to track the development of proprioceptive skills by a patient, so that the course of therapy can be monitored. In other embodiments, the quantitative feedback provided by the present system can be used to facilitate the selection of a prosthesis on the basis of the patient's proprioceptive response.

Additional advantages of the present invention may include a reduction of perceived real pain, as a result of distraction, and authentication of phantom perception.

While preferred embodiments of this invention have been shown and described, modifications thereof can be made by one skilled in the art without departing from the spirit or teachings of this invention. The embodiments described herein are exemplary only and are not limiting. Accordingly, the scope of protection is not limited to the embodiments described herein, but is only limited by the claims that follow, the scope of which shall include all equivalents of the subject matter of the claims.

What is claimed is:

1. A method for improving proprioception in a patient having a feedback site, comprising:
    affixing to the feedback site a sensor adapted to provide a sensor signal indicative of a sensed parameter;
    providing to the patient a signaler adapted to generate a manual signal in response to actuation by the patient;
    providing a microprocessor programmed to receive the sensor signal and the manual signal;
    causing the patient to actuate the signaler on the basis of sensation at the feedback site; and
    causing the microprocessor to generate a system output based on the sensor signal and the manual signal.

2. The method according to claim 1 wherein the sensor is a pressure sensor.

3. The method according to claim 1 wherein the system output is indicative of the difference between a target sensor signal and the value of the sensor signal at the time the manual signal is received.

4. The method according to claim 1 wherein the system output is indicative of the time elapsed between the manual signal and the time that the sensor signal reaches a predetermined target value.

5. The method according to claim 1, further including affixing a second sensor, wherein the system output is based signals from both sensors.

6. The method according to claim 5 wherein the system output is indicative of the position of the sensors relative to the patient.

7. The method according to claim 5 wherein the sensors affixed to the feedback site are mounted on a prosthetic foot.

8. The method according to claim 5 wherein the sensors affixed to the feedback site are mounted on a shoe.

* * * * *